(12) United States Patent
Stefanelli et al.

(10) Patent No.: US 9,549,902 B2
(45) Date of Patent: Jan. 24, 2017

(54) TRANSDERMAL PATCH

(75) Inventors: Paola Stefanelli, Milan (IT); Sergio Comuzio, Verdello (IT)

(73) Assignee: BOUTY S.P.A., Milan (IT)

( * ) Notice: Subject to any disclaimer, the term of this patent is extended or adjusted under 35 U.S.C. 154(b) by 1893 days.

(21) Appl. No.: 11/886,705

(22) PCT Filed: Mar. 22, 2006

(86) PCT No.: PCT/EP2006/060930
§ 371 (c)(1),
(2), (4) Date: Sep. 19, 2007

(87) PCT Pub. No.: WO2006/100251
PCT Pub. Date: Sep. 28, 2006

(65) Prior Publication Data
US 2009/0028929 A1    Jan. 29, 2009

(30) Foreign Application Priority Data

Mar. 23, 2005 (IT) .............................. MI2005A0477

(51) Int. Cl.
| | |
|---|---|
| *A61K 9/70* | (2006.01) |
| *A61K 31/121* | (2006.01) |
| *A61K 47/10* | (2006.01) |
| *A61K 47/26* | (2006.01) |
| *A61K 31/21* | (2006.01) |

(52) U.S. Cl.
CPC ............. *A61K 9/7061* (2013.01); *A61K 31/21* (2013.01); *A61K 47/10* (2013.01); *A61K 47/26* (2013.01)

(58) Field of Classification Search
CPC .... A61K 9/7061; A61K 31/121; A61K 47/10; A61K 47/26
See application file for complete search history.

(56) References Cited

U.S. PATENT DOCUMENTS 5,302,395 A * 4/1994 Ebert et al. .................... 424/449
6,231,885 B1 * 5/2001 Carrara ......................... 424/448

FOREIGN PATENT DOCUMENTS

| WO | WO 92/10154 A | 6/1992 |
|---|---|---|
| WO | WO 93/00058 A | 1/1993 |

OTHER PUBLICATIONS

Written Opinion from corresponding Application No. PCT/EP2006/060930 filed Mar. 22, 2005.

* cited by examiner

*Primary Examiner* — Rachael E Bredefeld
(74) *Attorney, Agent, or Firm* — Silvia Salvadori, P.C.; Silvia Salvadori

(57) ABSTRACT

A transdermal patch suitable for the administration of nitroglycerin.

4 Claims, No Drawings

TRANSDERMAL PATCH

FIELD OF THE INVENTION

The present invention relates to a transdermal patch for the administration of nitroglycerin.

STATE OF THE ART

Nitroglycerin is a vasodilator drug used in the prophylaxis and treatment of angina pectoris.

Because of its high capacity to permeate across the skin, this active principle is particularly suitable for transdermal administration.

In the last few years a number of transdermal systems have been developed for the administration of active principles. Of these, so-called drug-in-adhesive patches, which consist of a support layer and a drug/adhesive blend, have proved to be particularly advantageous largely from the production viewpoint. In these patches the drug is dispersed directly in the adhesive which then simultaneously carries out a number of functions. Indeed, in addition to maintaining the patch in close contact with the skin, the adhesive also acts as a reservoir for the drug and as a modulator for its release.

However, formulating drug-in-adhesive patches has the considerable drawback that the intrinsic properties of the polymer adhesive are modified by the addition of active principle and other possible components. High quantities of active principle, therefore, often lead to a loss in both adhesion and cohesion of the polymer and its capacity to control active principle release.

Consequently, drug-in-adhesive patches are characterised by a high ratio of adhesive quantity to active principle quantity, and, in order to achieve the release of adequate amounts of drug, they possess a large surface area which makes them not easy for the patient to use.

With the aim of overcoming this drawback, absorption enhancers are often used in the formulation of drug-in-adhesive patches, they being substances able to increase the permeability of skin to the active principle and so enable the active principle dose contained in the patch and the dimensions thereof to be reduced. In the case of nitroglycerin for example, the Minitran patch (3M Italia S.p.a.), which contains ethyl oleate as absorption enhancer, is that which, of commercially available nitroglycerin based transdermal patches, presents the most favourable ratio of active principle quantity contained to quantity released in vivo.

In particular Minitran enables a dosage of 15 mg/day of active principle to be administered via a formulation consisting of 54 g of nitroglycerin, 147 mg of acrylic acid copolymer derivative, 13 mg of ethyl oleate and 2.16 g of glyceryl monolaurate.

Patent EP0561983 describes a transdermal patch for administering nitroglycerin which contains a sorbitan ester as absorption enhancer. The author states that said patch is characterised by a very high permeation rate across the skin, being higher than that observed with Minitran.

The use of absorption enhancers however has the drawback of reducing patients' tolerance to the patch in that, as these substances interfere with the structure of the skin, they often give rise to skin irritation phenomena.

The need was therefore strongly felt to provide new transdermal formulations of nitroglycerin in which absorption enhancers would not be present and which would give rise to adequate plasma concentrations of principle without requiring the preparation of patches of excessive surface area.

SUMMARY OF THE INVENTION

The present inventors have now found a new formulation for the preparation of a drug-in-adhesive patch suitable for the administration of nitroglycerin that enables the permeation of an adequate quantity of nitroglycerin to be achieved without the need to use absorption enhancers.

In detail, the present invention provides a transdermal patch consisting of:
a) a backing layer impermeable to nitroglycerin; and
b) a matrix layer comprising:
   I) between 35% and 50% by weight, based on the dry mass, of nitroglycerin;
   II) between 40% and 80% by weight, based on the dry mass, of the self cross-linking acrylic acid/2-ethyl-acrylate/methyl-acrylate copolymer available commercially by the trade name Duro-Tak 87-2852;
   III) between 1.5% and less than 2.5% by weight, based on the dry mass, of sorbitan monooleate;
   IV) between 1% and 3% by weight, based on the dry mass, of propylene glycol.

Preferably, said matrix has a polymer:nitroglycerin ratio of at least 1:1.

The present inventors have surprisingly found, as will be demonstrated by the examples to follow, that despite sorbitan monooleate being described in patent EP0561983 as an absorption enhancer, this substance when present in the patch matrix in a quantity less than 2.5% by weight, does not act as an absorption enhancer but has the sole function of modulating the characteristics of the polymer adhesive.

The particular formulation of the invention surprisingly enables high doses of nitroglycerin to be incorporated into the patch without however interfering with its functional characteristics, particularly its adhesion capacity and capacity for release control.

Therefore, the patch of the invention enables satisfactory nitroglycerin permeation kinetics to be attained, without however the use of substances which can cause irritation, such as absorption enhancers.

DETAILED DESCRIPTION OF THE INVENTION

The present invention provides a transdermal patch of the drug-in-adhesive type suitable for administering nitroglycerin, comprising:
a) a backing layer impermeable to nitroglycerin, preferably consisting of low density polyethylene; and
b) a matrix layer comprising:
   I) between 35% and 50%, preferably between 40 and 45%, by weight, based on the dry mass, of nitroglycerin;
   II) between 40% and 80%, preferably between 50 and 55%, by weight, based on the dry mass, of the self cross-linking acrylic acid/2-ethyl-acrylate/methyl-acrylate copolymer available commercially by the trade name Duro-Tak 87-2852;
   III) between 1.5% and less than 2.5%, by weight, based on the dry mass, of sorbitan monooleate;
   IV) between 1% and 3% by weight, based on the dry mass, of propylene glycol.
   V) between 0% and 7.5% of other pharmacologically acceptable excipients.

Preferably, the matrix of the patch of the present invention has a polymer:nitroglycerin ratio of at least 1:1.

In accordance with a particularly preferred application, the matrix of the patch of the present invention presents the following percentage composition:
(I) between 43% and 44% by weight of nitroglycerin;
(II) between 52% and 53% by weight of self cross-linking acrylic acid/2-ethyl-acrylate/methyl-acrylate copolymer;
(III) between 1.5% and less than 2.5% by weight of sorbitan monooleate;
(IV) between 1 and 2% by weight of propylene glycol;
(V) between 0 and 2% of other pharmacologically acceptable excipients.

In accordance with a preferred embodiment, the patches of the present invention do not contain the excipients of group (V).

Preferably, the transdermal patches of the present invention have a dimension and composition such that a release of 5, 10 or 15 mg of nitroglycerin is achieved in 24 hours:

Particularly preferred embodiments of the transdermal patches of the present invention are the following:

Patch 1, in which the surface of the matrix to be applied to the skin has an area between 6 and 7.3 cm², preferably 6.7 cm², and the matrix has the following composition:
(I) between 24 and 29 mg, preferably 26.6 mg, of nitroglycerin;
(II) between 28.7 and 35.1 mg, preferably 31.9 mg of self cross-linking acrylic acid/2-ethyl-acrylate/methyl-acrylate copolymer;
(III) between 1.3 and 1.6 mg, preferably 1.5 mg, of sorbitan monooleate;
(IV) between 0.8 and 1.0 mg, preferably 0.9 mg, of propylene glycol.

The aforesaid patch is suitable for achieving a nitroglycerin release of 5 mg/24 hours, Patch 2, in which the surface of the matrix to be applied to the skin has an area between 12 and 14.6 cm², preferably 13.3 cm², and a matrix with the following composition:
(I) between 47.7 and 58.3 mg, preferably 53.0 mg, of nitroglycerin;
(II) between 57.1 and 69.8 mg, preferably 63.5 mg of self cross-linking acrylic acid/2-ethyl-acrylate/methyl-acrylate copolymer;
(III) between 2.7 and 3.3 mg, preferably 3 mg, of sorbitan monooleate;
(IV) between 1.5 and 1.9 mg, preferably 1.7 mg, of propylene glycol.

The aforesaid patch is suitable for achieving a nitroglycerin release of 10 mg/24 hours, Patch 3, in which the surface of the matrix to be applied to the skin has an area between 18 and 22 cm², preferably 20.0 cm², and the matrix has the following composition:
(I) between 72 and 88 mg, preferably 80 mg, of nitroglycerin;
(II) between 86.2 and 105.4 mg, preferably 95.8 mg of self cross-linking acrylic acid/2-ethyl-acrylate/methyl-acrylate copolymer;
(III) between 4 and 4.9 mg, preferably 4.5 mg, of sorbitan monooleate;
(IV) between 2.3 and 2.9 mg, preferably 2.6 mg, of propylene glycol.

The aforesaid patch is suitable for achieving a nitroglycerin release of 15 mg/24 hours.

The patches 1, 2 and 3 are bioequivalent to Minitrans patches but compared therewith they have the advantage of not containing any absorption enhancers and are therefore more tolerated by patients.

The present invention also provides a process for preparing said patches comprising the following steps:
a) preparing a semi-solid adhesive mass containing the active principle and all the other components of the matrix;
b) spreading the mass onto a siliconized support, for example siliconized polyester, to obtain a uniform and homogeneous film;
c) drying the film;
d) bonding the adhesive film to the backing;
e) cutting the patches into the desired shape and dimensions.

The aforesaid steps are carried out by following the procedures usually utilized for the preparation of drug-in-adhesive patches, well known to the expert of the art.

EXPERIMENTAL EXAMPLES

Example 1

Preparation of Patches Able to Release Respectively 5 mg, 10 mg and 15 mg of Nitroglycerin Per Day An adhesive semi solid mass with the following composition is prepared in a stainless steel mixer at ambient temperature:

| Raw material | Quantity % |
| --- | --- |
| Nitroglycerin diluted to 23% in Duro-Tak 87-2852 | 93.199 |
| Duro-Tak 87-2852 | 4.896 |
| Sorbitan oleate | 1.198 |
| Propylene glycol | 0.706 |

The mass obtained, transparent yellow in appearance, is left standing to enable any air incorporated during the stirring stage to be eliminated.

The adhesive mass containing the nitroglycerin is spread onto an industrial spreader in order to obtain a uniform and homogeneous film; a siliconized polyester liner is used as the spreading support, which will form the final protective layer for the patch. The gap between the rollers, which determine the mass dispensed, is regulated as a function of the weight of the dried mass which must be equal to 91.32 g/m²; this quantity of dried mass corresponds to a nitroglycerin concentration of 39.9 g/m².

Directly after this step, the solvent is evaporated by means of drying in forced air ovens.

At the end of the drying process, the film with the liner is bonded to the low density polyethylene backing and wound into master rolls; the different affinity the adhesive film has with the liner compared to the backing enables transfer and anchorage of the adhesive onto this latter.

The master rolls obtained are cut into bobbins whose dimensions vary according to the final patch dosage.

The bobbins thus cut are loaded onto the forming machine which punches out the patches according to the specifications of the desired shape as shown in the following table:

| Dosage | Dimensions of punch | Dimensions of patch |
|---|---|---|
| 5 mg/24 hours | 45 × 45 mm | 6.67 cm$^2$ |
| 10 mg/24 hours | 45 × 30 mm | 13.285 cm$^2$ |
| 15 mg/24 hours | 27 × 25.5 mm | 20.035 cm$^2$ |

Following production each individual unit is primary packaged.

In the secondary packaging 15 patches and an instruction leaflet are placed in a cardboard box.

Example 2

In Vitro Analysis of Nitroglycerin Permeation Kinetics

With the purpose of analysing the effect of sorbitan monooleate on nitroglycerin permeation kinetics, permeation of nitroglycerin from transdermal patches containing different concentrations of sorbitan monooleate was measured across mouse skin and human skin in Franz diffusion cells (produced by Hanson-Research).

The test was undertaken as described in the Italian Official Pharmacopoeia XI ed. and the European Pharmacopoeia 4$^{th}$ ed.

In detail, two patches having the following formulas were prepared, expressed as weight percentages of the single components:

|  | Patch A | Patch B |
|---|---|---|
| Nitroglycerin | 43.74% | 44.84% |
| Duro-Tak 87-2852 | 52.37% | 53.69% |
| Sorbitan oleate | 2.44 | 0 |
| Propylene glycol | 1.44 | 1.48 |

2a) Permeation Studies Across Mouse Skin

The permeation studies were conducted using Franz diffusion cells modified with an aperture 15 mm in diameter (membrane surface area 1.766 cm$^2$) and 7 ml cell volume. A phosphate buffer at pH 7 maintained under constant agitation was used as receptor fluid within the cell.

CDF1 mice aged 6 weeks at the most were killed and samples of skin taken from their backs were depilated and washed in physiological solution (0.9% NaCl in distilled water).

Within an hour of removal from the animal the skin samples were placed over the aperture of the cells to form a membrane and the transdermal patches to be analysed were each placed over a membrane and fastened with clips.

At determined intervals 300 μl of receptor solution were withdrawn and replaced each time with an equivalent volume of phosphate buffer.

The conditions under which the permeation test was carried out are summarized in the following table:

| Dimensions of patch | 1.766 cm$^2$ |
|---|---|
| Receptor solution | Phosphate buffer at pH 7.4 |
| Volume | 7 ml |
| Temperature | 37° C. |
| Times of sample withdrawal | 2 h, 4 h, 6 h, 8 h, 24 h |

The quantity of nitroglycerin in each sample was determined by means of HPLC analysis, using a 50:50 methanol/water mixture as mobile phase.

The results obtained for each patch are shown in the following tables:

| PATCH A | | | | | |
|---|---|---|---|---|---|
| | Cumulative quantity (μg/cm$^2$) | | | | |
| | 2 h | 4 h | 6 h | 8 h | 24 h |
| Mean | 8.7 | 36.3 | 78.7 | 130.1 | 782.5 |
| Std Dev. | 5 | 17.3 | 35.3 | 46.3 | 198.8 |

| PATCH B | | | | | |
|---|---|---|---|---|---|
| | Cumulative quantity (μg/cm$^2$) | | | | |
| | 2 h | 4 h | 6 h | 8 h | 24 h |
| Mean | 9 | 38.7 | 83.9 | 143.2 | 763.2 |
| Std Dev. | 2.6 | 8.2 | 17.1 | 26.8 | 121.3 |

The results obtained for each patch were analyzed statistically using the t-test for independent samples.

The results of the t-test are given in the following table and indicate that there are no significant differences between skin permeation kinetics obtained with patches A and B

| Group 1 | Group 2 | Mean of group 1 (μg/cm$^2$/h) | Mean of group 2 (μg/cm$^2$/h) | Value of t | P |
|---|---|---|---|---|---|
| Patch B | Patch A | 35.6 | 36.7 | −0.2423 | 0.8135 |

The steady-state flux was then determined for each patch by means of linear regression of the cumulative quantity of drug permeated across the skin (μg/cm$^2$) as a function of time (h), to obtain the following results.

| | Flux (μg/cm$^2$/h) |
|---|---|
| Patch A | 36.7 ± 9.0 |
| Patch B | 35.6 ± 5.6 |

The results obtained show that the permeation rates of nitroglycerin across skin obtained with the two patches compared in this study are very similar.

Consequently the permeation observed by a patch whose matrix contains 2.44% of sorbitan monooleate is equivalent to that observed with a patch which does not contain sorbitan monooleate. Therefore, the results of our study show that at the concentrations analysed the sorbitan monooleate does not act as an absorption enhancer.

2b) Studies of Permeation Across Human Skin

Samples of abdominal skin were obtained from the same donor by means of a surgical procedure.

Membranes consisting of the stratum corneum and epidermis (SCE membranes) were prepared by immersing the skin into distilled water at 60° C.±1° C. for one minute followed by their removal from the dermis. The membranes were dried in a dryer at about 25% ambient humidity, wrapped in aluminium sheets and maintained at a temperature of about −20° C.±1° C. until required. Dried membrane samples were rehydrated at ambient temperature by immersing in a saline solution for 16 hours.

Each membrane was then mounted onto modified Franz diffusion cells, having a receptor volume of 5 ml and diffusion area of 0.636 cm$^2$, and fastened by means of clips.

At the start of the experiment, patches having an area of 2.54 cm$^2$ were applied to the diffusion cell as the donor phase.

The receptor liquid consisted of a phosphate buffer at pH 7.4, continuously stirred with a magnetic stirrer and temperature controlled at 37° C.±1° C., so that the surface of the skin was at a temperature of 32°±1° C. At pre-established intervals (1 h, 3 h, 5 h, 8 h and 24 hours) 200 µl samples were withdrawn from the receptor compartment and replaced with fresh receptor fluid.

The quantitative results obtained for each cell are shown in the following tables:

| PATCH A | | | | | |
|---|---|---|---|---|---|
| | Cumulative quantity (µg/cm$^2$) | | | | |
| | 1 h | 3 h | 5 h | 8 h | 24 h |
| Mean | 16.23 | 48.99 | 81.39 | 132.45 | 419.68 |
| Std Dev. | 2.41 | 4.54 | 13.46 | 18.11 | 75.93 |

| PATCH B | | | | | |
|---|---|---|---|---|---|
| | Cumulative quantity (µg/cm$^2$) | | | | |
| | 1 h | 3 h | 5 h | 8 h | 24 h |
| Mean | 16.52 | 49.36 | 80.24 | 120.64 | 360.40 |
| Std Dev. | 5.98 | 17.00 | 26.90 | 32.20 | 115.49 |

The results obtained were analysed statistically using the t-test for independent samples.

The results of the t-test are given in the following table and indicate that there are no significant differences between skin permeation kinetics obtained with patches A and B.

| Group 1 | Group 2 | Mean of group 1 (µg/cm$^2$/h) | Mean of group 2 (µg/cm$^2$/h) | Value of t | P |
|---|---|---|---|---|---|
| Patch B | Patch A | 14.8700 | 17.6267 | 1.227 | 0.275 |

The steady-state flux was then determined for each patch by linear regression of the cumulative quantity of drug permeated across the skin (µg/cm$^2$) as a function of time (h). The results obtained, shown in the following table, confirm that there are no significant differences between the two patches.

However the tests undertaken on human skin also confirm that sorbitan monooleate at the tested concentrations does not act as an absorption enhancer.

| | Flux (µg/cm$^2$/h) |
|---|---|
| Patch A | 17.63 ± 3.42 |
| Patch B | 14.87 ± 4.43 |

The invention claimed is:

1. A drug-in-adhesive type transdermal patch comprising:
   a) a backing layer impermeable to nitroglycerin; and
   b) a matrix layer consisting essentially of:
   (I) between 40% and 45% by weight, based on the dry mass, of nitroglycerin;
   (II) between 50% and 55-% by weight, based on the dry mass, of self-cross-linking acrylic acid/2-ethyl-acrylate/methyl-acrylate copolymer;
   (III) between 1.5% and 2.5% by weight, based on the dry mass, of sorbitan monooleate;
   (IV) between 1% and 3% by weight, based on the dry mass, of propylene glycol; and
   (V) between 0% and 7.5% by weight of other pharmacologically acceptable excipients,
   wherein no absorption enhancers are present in the patch.

2. The patch as claimed in claim 1, wherein said matrix layer presents the following percentage composition:
   (I) between 43% and 44% by weight, based on the dry mass, of nitroglycerin;
   (II) between 52% and 53% by weight, based on the dry mass, of self cross-linking acid/2-ethyl-acrylate/methyl-acrylate copolymer;
   (III) between 1.5% and 2.5% by weight of sorbitan monooleate;
   (IV) between 1% and 2-% by weight of propylene glycol; and
   (V) between 0% and 2-% by weight of other pharmacologically acceptable excipients.

3. The patch as claimed in claim 1, wherein the excipients of group V are not present.

4. A process for preparing the patch as claimed in claim 1, comprising the following steps:
   a) preparing a semi-solid adhesive mass containing the nitroglycerin and all the other components of the matrix layer;
   b) spreading the mass onto a siliconized support to obtain a uniform and homogeneous film;
   c) drying the film;
   d) bonding the adhesive film to a backing; and
   e) cutting the adhesive film on the backing into a desired shape and dimensions.

* * * * *